United States Patent [19]

Massonneau et al.

[11] Patent Number: 4,925,949

[45] Date of Patent: May 15, 1990

[54] PROCESS FOR PREPARING 1-ALKYL-5-NITROIMIDAZOLES

[75] Inventors: Viviane Massonneau; Michel Mulhauser, both of Ecully; Claude Bonnamas, Commentry; Noël Rouy, Yerres, all of France

[73] Assignee: Rhone-Poulenc Sante, Antony, France

[21] Appl. No.: 296,709

[22] Filed: Jan. 13, 1989

[30] Foreign Application Priority Data

Jan. 15, 1988 [FR] France ............................. 88 00414
Jun. 10, 1988 [FR] France ............................. 88 07773

[51] Int. Cl.$^5$ ................... C07D 233/92; C07D 405/06
[52] U.S. Cl. ..................................... 548/336; 548/338; 548/339; 548/340
[58] Field of Search ............... 548/338, 336, 339, 340

[56] References Cited

FOREIGN PATENT DOCUMENTS

| 043922 | 1/1982 | European Pat. Off. |
| 072919 | 3/1983 | European Pat. Off. |
| 1216238 | 4/1960 | France. |
| 2265743 | 10/1975 | France. |
| 2263241 | 4/1977 | France. |

OTHER PUBLICATIONS

Fieser, L. et al., *Reagents for Organic Synthesis*, John Wiley, New York, 1967, pp. 294–295.

*Chemical Abstracts*, 77:139490t (1972) [D. Tomalia et al., *J. Heterocycl. Chem.*, 1972, 9(4), 891–4].

*Primary Examiner*—Richard A. Schwartz
*Attorney, Agent, or Firm*—Stevens, Davis, Miller & Mosher

[57] ABSTRACT

Process for preparing 1-alkyl-5-nitroimidazoles of formula:

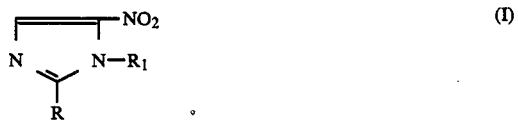

which comprises reacting an alkyl sulphate with an imidazole derivative of general formula:

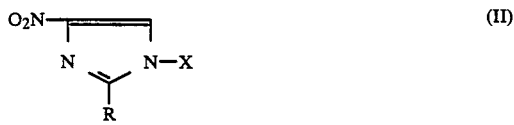

in an organic solvent, and then hydrolyzing or alcoholyzing the product obtained. In the formulae (I) and (II), R denotes hydrogen, unsubstituted or substituted alkyl, aryl or cycloalkyl. In the formula (I), $R_1$ denotes alkyl. In the formula (II), X denotes a group which can be removed by hydrolysis or alcoholysis.

5 Claims, No Drawings

PROCESS FOR PREPARING 1-ALKYL-5-NITROIMIDAZOLES

The present invention provides a process for preparing 1-alkyl-5-nitroimidazoles of formula:

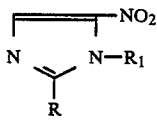
(I)

in which
R denotes hydrogen or alkyl of 1 to 4 carbon atoms or alkenyl of 2 to 4 carbon atoms, the said alkyl and alkenyl radicals being unsubstituted or substituted by one or more identical or different radicals chosen from phenyl, phenoxy, and 5- or 6-membered oxygen-containing heterocyclic radicals;
or alternatively R denotes aryl of 6 to 10 carbon atoms, unsubstituted or substituted with one or more identical or different substituents chosen from halogen, alkyl of 1 to 4 carbon atoms, alkoxy of 1 to 4 carbon atoms, phenyl, phenoxy, and nitro;
or alternatively R denotes cycloalkyl of 5 or 6 carbon atoms, the aforesaid phenyl, phenoxy or heterocyclic radicals being unsubstituted or substituted by one or more identical or different substituents chosen from halogen, alkyl of 1 to 4 carbon atoms, alkoxy of 1 to 4 carbon atoms, phenyl, phenoxy, and nitro;
and $R_1$ denotes alkyl of 1 to 12 carbon atoms in a straight or branched chain.

In French Patent Application 75/09,065 (published as 2,265,743) a process has been described for preparing 1-alkyl-5-nitroimidazole derivatives by the action of an alkyl sulphate of formula:

in which $R_1$ is defined as above, on an imidazole derivative of formula:

(III)

in which R is defined as above, in the presence of a carboxylic acid.

According to the present invention, the imidazole derivatives of formula (I) are obtained by a process which comprises: reacting an alkyl sulphate of general formula (II) with an imidazole derivative of formula:

(IV)

in which R is defined as above and X denotes a group which can be readily removed by hydrolysis or alcoholysis, in an organic solvent; and hydrolysing or alcoholysing the product optionally in situ.

In the formula (IV), X may denote a hydroxymethyl radical, an alkoxymethyl radical in which the alkyl portion contains 1 to 4 carbon atoms, an acyloxymethyl radical in which the acyl portion contains 1 to 4 carbon atoms, an allylic ethylenic radical such as allyl or an arylmethyl radical such as benzyl.

In general, the process is carried out at a temperature from 60° to 120° C., and preferably in the region of 80° C.

As an organic solvent, esters (methyl acetate, ethyl acetate), ethers (methyl tert-butyl ether) or aliphatic or aromatic halogenated or unhalogenated hydrocarbons (xylene, methylene chloride), are preferably used.

In general, the hydrolysis or alcoholysis of the condensation product is performed by heating in water or an alcohol (methanol, ethanol) to a temperature from 60° to 100° C. It is not necessary to isolate the condensation product prior to the hydrolysis.

The imidazole derivatives of formula (IV) may be prepared under the conditions described in British Patent GB 1,026,631.

The imidazole derivatives of formula (I) possess therapeutic properties, or constitute intermediates for the preparation of dyes, adjuvants for textiles or insecticides.

The examples which follow show how the invention may be put into practice.

EXAMPLE 1

1-Acetoxymethyl-2-methyl-4-nitroimidazole (3.98 g; 0.02 mole) and xylene (10 cc) are introduced into a round-bottomed flask equipped with a stirrer and a dropping funnel. The mixture is heated to 80° C. and methyl sulphate (3.2 g; 0.024 mole) is then introduced. The mixture is heated to 80° C. for 2 hours. Water (25 cc) is then added and the mixture is thereafter heated to 80° C. for 2 hours 30 minutes.

After dilution, analysis of the reaction medium by high performance liquid chromatography shows that it contains 1,2-dimethyl-5-nitroimidazole (2.8 g).

The degree of conversion of 2-methyl-4(or 5)-nitroimidazole is in the region of 100%.

The yield of 1,2-dimethyl-5-nitroimidazole is greater than 95% relative to the 1-methyl-4(or 5)-nitroimidazole introduced.

EXAMPLE 2

Xylene (20 cc) is introduced into a 50 cc three-necked round-bottomed flask, 1-acetoxymethyl-4-nitroimidazole (3.7 g) is then added and the mixture is then heated to 80° C. The "melting" of the 1-acetoxymethyl-4-nitroimidazole and the formation of two phases are observed. Dimethyl sulphate (2.52 g) is added in the course of 30 minutes at 80° C. The reaction mixture, consisting of 2 colourless phases, is heated to 80° C. for 1 hour. After the mixture is cooled to 70° C., water (20 cc) is added and the mixture is stirred for 3 hours 30 minutes at this temperature.

Assay of the reaction mixture by high performance liquid chromatography (HPLC) shows that:
the degree of conversion of 1-acetoxymethyl-4-nitroimidazole is 92%
the yield of 1-methyl-5-nitroimidazole is 83%.

EXAMPLE 3

The procedure is as in Example 2, but at a temperature of 100° C. After hydrolysis for 1 hour 30 minutes under reflux, followed by cooling to a temperature in the region of 20° C., the aqueous phase is separated off after settling has occurred and the xylene phase is washed with water (3×20 cc).

The combined aqueous phases, assayed by HPLC, show that:

the degree of conversion of 1-acetoxymethyl-4-nitroimidazole is 94.6% the yield of 1-methyl-5-nitroimidazole is 87.2%.

We claim:

1. A process for preparing 1-alkyl-5-nitroimidazoles of formula:

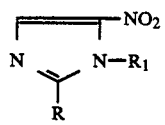

in which

R denotes hydrogen, alkyl of 1 to 4 carbon atoms or alkenyl of 2 to 4 carbon atoms, the said alkyl and alkenyl radicals being unsubstituted or substituted by one or more identical or different radicals chosen from phenyl, phenoxy and 5- or 6-membered oxygen-containing heterocyclic radicals;

or alternatively R denotes aryl of 6 to 10 carbon atoms, unsubstituted or substituted by one or more identical or different substituents chosen from halogen, alkyl of 1 to 4 carbon atoms, alkoxy of 1 to 4 carbon atoms, phenyl, phenoxy, and nitro;

or alternatively R denotes cycloalkyl of 5 or 6 carbon atoms; the aforesaid phenyl, phenoxy and heterocyclic radicals being unsubstituted or substituted by one or more identical or different substituents chosen from halogen, alkyl of 1 to 4 carbon atoms, alkoxy of 1 to 4 carbon atoms, phenyl, phenoxy, and nitro;

and $R_1$ denotes alkyl of 1 to 12 carbon atoms in a straight or branched chain, which comprises: reacting an alkyl sulphate of formula:

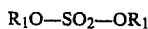

in which $R_1$ is defined as above, with an imidazole derivative of formula:

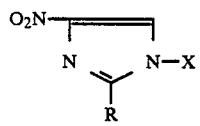

in which R is defined as above and X denotes a group which can be readily removed by hydrolysis or alcoholysis, in an organic solvent, and hydrolysing or alcoholysing the product obtained.

2. A process according to claim 1, wherein the hydrolysis or alcoholysis is performed in situ.

3. A process according to claim 1, wherein the group which can be removed by hydrolysis or alcoholysis is a hydroxymethyl radical, an alkoxymethyl radical in which the alkyl portion contains 1 to 4 carbon atoms, an acyloxymethyl radical in which the acyl portion contains 1 to 4 carbon atoms, an allylic ethylenic radical or an arylmethyl radical.

4. A process according to claim 1, wherein the reaction is performed in an ester, ether or aliphatic or aromatic halogenated or unhalogenated hydrocarbon.

5. A process according to claim 1, wherein the reaction is performed at a temperature from 60° to 120° C.

* * * * *